Dec. 6, 1960 K. R. KERNS ET AL Plant Pat. 1,993
PINEAPPLE PLANT
Filed July 6, 1959
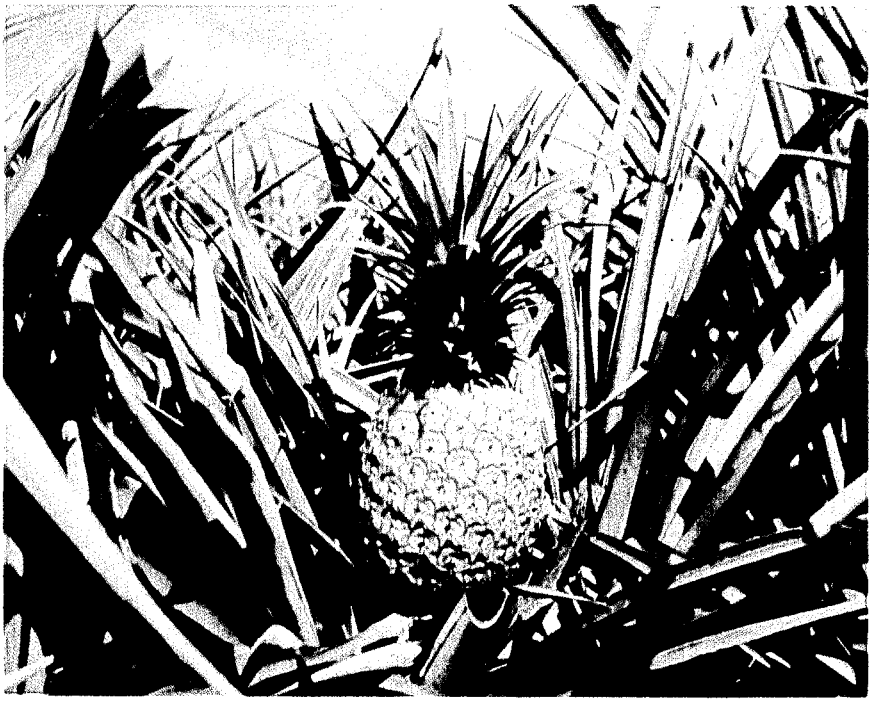
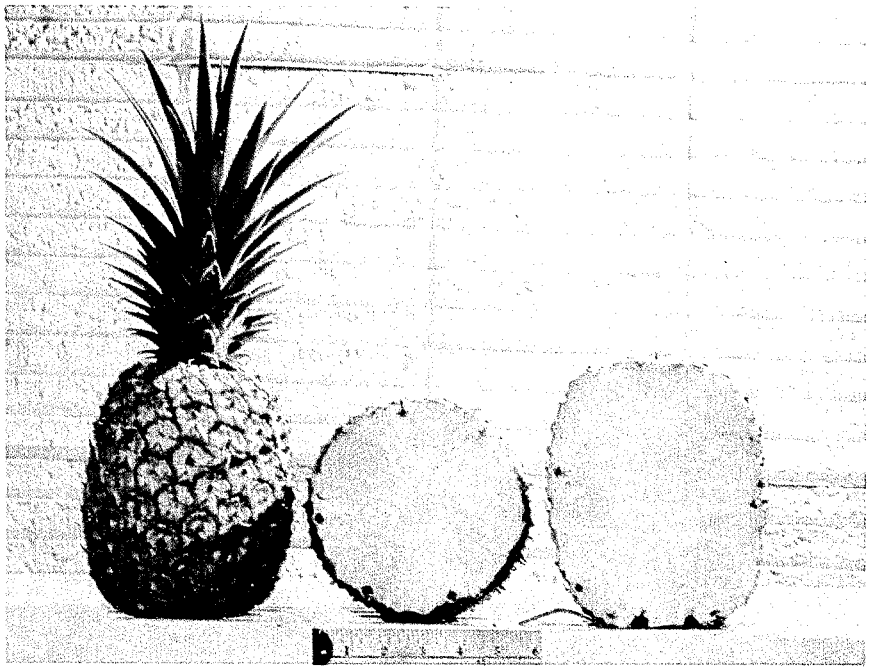
Kenneth R. Kerns
J. Lloyd Collins United States Patent Office Plant Pat. 1,993
Patented Dec. 6, 1960

1,993

PINEAPPLE PLANT

Kenneth R. Kerns, Wahiawa, Hawaii, and Julius Lloyd Collins, Alpine, Calif., assignors to Pineapple Research Institute of Hawaii, Honolulu, Hawaii Filed July 6, 1959, Ser. No. 825,382

1 Claim. (Cl. 47—62)

The present invention relates to a new and distinct variety of pineapple which was developed by us in the following manner.

In March 1930, the Red Spanish variety of pineapple was crossed with the Cayenne variety of pineapple as the female parent. Both varieties are self-incompatible. The seeds of the cross were germinated under lot Number 669 on January 30, 1931. Germination of the seeds was satisfactory and after some green house elimination 3,136 plants of lot 669 were planted to the field. This lot of seedlings was fruiting as plant crop in 1933 and as first ratoon in 1934. The instant variety was selected as one of the 3,136 plants of lot 669 on September 24, 1934. The original selection of the instant variety was 10,388.

The varieties "Red Spanish" and "Cayenne" have no plant patent numbers. These are old established varieties in the trade and were described in the Fla. Agr. Exp. Sta. Bul. 70, Hume, H. H. and K. H. Miller, 1904. More recently both parent varieties are described in The Pineapple, Botany, Cultivation and Utilization, J. L. Collins, published by Leonard Hill Book Company, London.

After the initial discovery of the instant variety, we promptly took steps to preserve and asexually propagate the same. All increase planting materials were crowns, slips and suckers (propagative buds of the pineapple plant) derived from the original plant. This propagation was at the Pineapple Research Institute at Wahiawa, Oahu, Hawaii. Continued observation and testing of the new variety by us established that the new variety had distinctive characteristics which come true to form and are established and transmissible through succeeding propagations.

While the internal characteristics of the fruit of our new variety more nearly resemble the Red Spanish parent, the fruit yields are comparable to the Cayenne variety and are a distinct commercial advantage over the yields of the Red Spanish variety. In addition, our new variety has extreme resistance to soil borne heart and root rot (*Phytophthora cinnamoni*) that is a distinct advantage over the Cayenne variety. In Table 2 is presented the percent of plants lost to heart rot and the reduced vigor of the plants as a measure of root rot, with yields of fruit and planting materials when our new variety was grown in an area infested with the soil borne heart and root rot fungus *Phytophthora cinnamoni*. This test was conducted in the Helemano area of Oahu, Hawaii, on soil so badly infested with *Phytophthora cinnamoni* as to be eliminated for commercial production of pineapple. These are distinctive features which constitute substantial improvements over either parent variety alone and represent exceedingly desirable charatceristics from the commercial standpoint.

The accompanying drawing shows typical specimens of the fruit and foliage of our new variety. All is depicted in color as nearly true as it is reasonably possible to make the same in color illustration of this character, with one view showing the variety in the field and the other view showing a cross and longitudinal section of a typical fruit specimen showing a cross and longitudinal section of a typical fruit specimen.

The following is a detailed description of our new variety with color description in accordance with the Horticulture Colour Guide, except where general color terms of ordinary dictionary significance are obvious.

Observations made from specimens grown near Wahiawa, Island of Oahu, Hawaii.

PLANT

*Maturity.*—Fruit of the instant variety ripens 20–25 days later than the Cayenne variety.

*Habit.*—The variety is hardy and resembles the Red Spanish parent in color and habit of growth. A typical well grown plant 22 months of age weighed 8.5 lbs., green weight.

*Leaves.*—The above mentioned plant had 46 functional green leaves of which the longest was 3.9 feet. The greatest width of the longest leaf was 2.4 inches. There is a variable quantity of reddish anthocyanin pigment overlaying the green coloring of the leaf. The green color of the top surface of the leaf is Parsley Green, Plate 00962/c, p. 193, vol. II, Horticulture Colour Guide. The underside of the leaf has bloom from the trichomes and is lavender Green, Plate 000761/2, p. 196, vol. II, of the Horticulture Colour Guide.

The leaves are smooth with irregular small spines at the tip, extending down 10 inches. The spines all point to the tip and are reddish tinged in color.

The leaves more closely resemble the Red Spanish parent, being slightly darker green and narrower than the leaves of the Cayenne parent.

*Stem.*—The above mentioned plant had a plane stem (stump) 11.5 inches in length which weighed 1.6 pounds. The fruit stem (peduncle) was 9 inches in length. There is some variation in plant size, plant stem (stump), peduncle length and resulting leaf number, depending on plant growth.

FLOWERS

The petals have a bluish tinge with the exposed portion being color Dauphin's Violet, Plate 039/1, p. 117, vol. II, Horticulture Colour Guide.

FRUIT

*Maturity when described.*—Canning ripe.

*External characteristics.*—A typical fruit with a weight of 5 pounds exclusive of the crown had 128 eyes. This is considerably more than the Red Spanish parent. The eyes are rather rectangular, flat, ¾ x ⅞ inch to 1 x 1⅝ inches in width and length respectively. The eye bracts are yellow to salmon pink covering one-third of the eye and projecting to the nipple. The overall eye color is Spanish Orange, Plate 010/2, p. 103, vol. II, Horticulture Colour Guide. The fruit, having more eyes than the Red Spanish parent, does not exhibit the growth cracks between the eyes that is common for the Red Spanish variety when grown in Hawaii.

The fruit shape is cylindrical, with square shoulders, being an improvement on both the Red Spanish and Cayenne parents. The diameter is comparatively large for the length of fruit. The length of the above mentioned 5 pound fruit was 7⅛ inches, exclusive of the crown, and diameter was 6⅛ inches.

*Internal characteristics.*—Internally the variety resembles the Red Spanish parent in color. Pigment analyses in parts per million carotene of the fresh fruit revealed:

| | |
|---|---|
| The instant variety | 0.28 |
| Red Spanish parent | 0.29 |
| Cayenne parent | 1.66 |

These values are averages of 4 replicate samples analyzed in Hawaii on March 12, 1959.

*Flesh color.*—The flesh color in the Horticulture Colour Guide is Primrose Yellow, Plate 601/3, page 65, vol. I.

*Brix and acid.*—The fruit is juicy with the aroma of the Red Spanish parent. The average summer Brix value of the variety when grown near Wahiawa, Oahu, Hawaii, is about 13.5 and acidity is about 0.82 percent.

*Texture.*—The texture resembles the Cayenne parent with less fibrousness than the Red Spanish parent.

*Incidence of fruit disease.*—The incidence of fruit disease is low, being no more than that found in the Cayenne parent and much less than that of the Red Spanish parent in Hawaii.

*Flavor.*—The flavor resembles that of the Red Spanish variety.

*Core.*—The core of the 5 pound fruit described above was 1⅛ inches in width, approximately that of the Cayenne parent.

*Slice pattern.*—The pattern of the carpels is inconspicuous in canned slices.

CROWN

The crown has stiff upright leaves and is slightly larger than the crown of the Cayenne parent. A 7½ ounce crown from the above mentioned 5 pound fruit had leaves 9 inches in length. The crown and well developed slips and suckers make excellent planting material.

YIELD

The yield performance of the instant variety on the island of Oahu, near the town of Wahiawa (Table 1), a typical pineapple growing area, and the yield performance in a severe heart and root rot area on Oahu, Hawaii (Table 2), are presented below.

*Table 1.—Exhibit of yield of the instant variety in comparison with the Cayenne variety for 5 plant crop years and 2 ratoon crops. Wahiawa, Hawaii*

| Year | Planting Material | Av. Fruit Wt. | | Av. Number | | Fruit | |
|---|---|---|---|---|---|---|---|
| | | Lbs. | Percent Cayenne | Slips | Suckers | Brix | Acid |
| 1950 | Slips | 5.29 | 99 | 3.88 | 1.42 | 13.6 | 0.78 |
| 1952 | do | 5.38 | 108 | 2.44 | 2.50 | 13.1 | 0.73 |
| 1954 | do | 4.65 | 99 | 1.82 | 1.52 | 13.7 | 0.83 |
| 1956 | do | 5.17 | | 2.08 | 1.98 | 13.8 | 0.86 |
| 1957 | Crowns | 4.77 | 102 | 1.90 | 1.61 | 13.4 | 0.92 |
| 1958 | do | [1] 4.69 | 120 | | | 13.6 | 0.76 |
| 1957 | Suckers | 5.06 | 126 | 1.77 | 1.77 | 13.5 | 0.84 |
| 1958 | do | [1] 4.56 | 113 | | | 14.2 | 0.76 |

[1] First ratoon.

*Table 2.—Exhibit of yield of the instant variety and the Cayenne parent in a severe heart and root rot area. Harvested 1958. Helemano, Oahu, Hawaii.*

| Variety | Percent Dead from Heart Rot | Vigor Rating [1] | Harvested Frt.[2], Tons per acre | Av. No./plant | |
|---|---|---|---|---|---|
| | | | | Slips | Suckers |
| The instant variety | 0.0 | 1.4 | 30.8 | 2.63 | 1.37 |
| Cayenne (parent) | 13.6 | 2.3 | 19.7 | 1.51 | 1.54 |

[1] Vigor rating: 1—normal growth; 2,3,4—successively weaker; 5—all dead.
[2] Calculated from actual harvested fruits in an experiment replicated 10 times, plot size 10 plants.

We claim:

A new and distinct variety of pineapple plant, substantially as herein shown and described, characterized particularly as to novelty by its general internal fruit characteristics resembling the Red Spanish parent, and the yield characteristics of the larger yielding Cayenne parent. In addition, our new variety has extreme resistance to heart and root rot caused by *Phytophthora cinnamoni.*

No references cited.